United States Patent
Song et al.

(10) Patent No.: US 11,748,849 B2
(45) Date of Patent: Sep. 5, 2023

(54) SYSTEMS AND METHODS FOR KALMAN FILTER-BASED MICROVESSEL INPAINTING FOR SUPER-RESOLUTION IMAGING

(71) Applicant: Mayo Foundation for Medical Education and Research, Rochester, MN (US)

(72) Inventors: Pengfei Song, Champaign, IL (US); Shigao Chen, Rochester, MN (US); Joshua D. Trzasko, Rochester, MN (US); Armando Manduca, Rochester, MN (US); Shanshan Tang, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 215 days.

(21) Appl. No.: 17/286,681

(22) PCT Filed: Oct. 18, 2019

(86) PCT No.: PCT/US2019/056903
§ 371 (c)(1),
(2) Date: Apr. 19, 2021

(87) PCT Pub. No.: WO2020/081915
PCT Pub. Date: Apr. 23, 2020

(65) Prior Publication Data
US 2021/0374910 A1     Dec. 2, 2021

Related U.S. Application Data

(60) Provisional application No. 62/747,990, filed on Oct. 19, 2018.

(51) Int. Cl.
*G06K 9/00*     (2022.01)
*G06T 3/40*     (2006.01)
(Continued)

(52) U.S. Cl.
CPC .......... *G06T 3/4053* (2013.01); *A61B 8/0891* (2013.01); *A61B 8/481* (2013.01);
(Continued)

(58) Field of Classification Search
None
See application file for complete search history.

(56) References Cited

U.S. PATENT DOCUMENTS

2003/0229285 A1   12/2003  Simpson

FOREIGN PATENT DOCUMENTS

| CN | 107753062 A | 3/2018 |
|----|----|----|
| WO | 2018222724 A1 | 12/2018 |

OTHER PUBLICATIONS

Solomon, Oren, et al. "Exploiting flow dynamics for super-resolution in contrast-enhanced ultrasound." arXiv e-prints (2018): arXiv-1804. (Year: 2018).*

(Continued)

*Primary Examiner* — Avinash Yentrapati
(74) *Attorney, Agent, or Firm* — Quarles & Brady LLP

(57) ABSTRACT

Described here are systems and methods for super-resolution imaging with ultrasound in which a Kalman filter-based microvessel inpainting technique is used to facilitate robust super-resolution imaging with limited or otherwise missing microbubble signals. The systems and methods described in the present disclosure can be combined with both local and global microbubble tracking methods.

17 Claims, 5 Drawing Sheets

(51) Int. Cl.
G06T 7/277 (2017.01)
A61B 8/08 (2006.01)
G01S 7/52 (2006.01)
G01S 15/89 (2006.01)
G06T 5/00 (2006.01)

(52) U.S. Cl.
CPC ...... *G01S 7/52026* (2013.01); *G01S 7/52041* (2013.01); *G01S 15/89* (2013.01); *G06T 3/4007* (2013.01); *G06T 5/002* (2013.01); *G06T 7/277* (2017.01); *G06T 2207/10132* (2013.01); *G06T 2207/20182* (2013.01); *G06T 2207/30101* (2013.01)

(56) References Cited

OTHER PUBLICATIONS

Christensen-Jeffries, K., et al.. In vivo acoustic super-resolution and super-resolved velocity mapping using microbubbles. IEEE Trans Med Imaging, 2015. 34(2): p. 433-40.

Errico, C., et al., Ultrafast ultrasound localization microscopy for deep super-resolution vascular imaging. Nature, 2015. 527: p. 499.

International Searching Authority. International Search Report and Written Opinion for application PCT/US2019/056903. dated Jan. 2, 2020. 12 pages.

Murphy, K. 2004. Kalman Filter Toolbox for Matlab. Available online at https://www.cs.ubc.ca/~murphyk/Software/Kalman/kalman.html.

Solomon, O., et al. "Exploiting flow dynamics for super-resolution in contrast-enhanced ultrasound." arXiv.org, Cornell University Library, 201 Olin Library Cornell University Ithaca, MY 14853 preprint arXiv:1804.03134 (2018).

Song, P. et al. "Improved super-resolution ultrasound microvessel imaging with spatiotemporal nonlocal means filtering and bipartite graph-based microbubble tracking." IEEE transactions on ulliasonics, ferroelectrics, and frequency control 65.2 (2017): 149-167.

Song, P. et al. Kalman Filter-based Microvessel Inpainting for Super-Resolution Imaging. Abstract 3G-5.IEEE International Ultrasonics Symposium Abstract Book. Sep. 19, 2018.

* cited by examiner

SYSTEMS AND METHODS FOR KALMAN FILTER-BASED MICROVESSEL INPAINTING FOR SUPER-RESOLUTION IMAGING

CROSS-REFERENCE TO RELATED APPLICATIONS

This application is a 371 U.S. National Phase application of PCT/US2019/056903, filed Oct. 18, 2019, which claims the benefit of U.S. Provisional Patent Application Ser. No. 62/747,990, filed on Oct. 19, 2018, and entitled "SYSTEMS AND METHODS FOR KALMAN FILTER-BASED MICROVESSEL INPAINTING FOR SUPER-RESOLUTION IMAGING," which is herein incorporated by reference in its entirety.

STATEMENT REGARDING FEDERALLY SPONSORED RESEARCH

This invention was made with government support under CA214523 awarded by the National Institutes of Health. The government has certain rights in the invention.

BACKGROUND

A common challenge in microbubble-based super-resolution imaging is the long accumulation time needed for adequate microbubbles to populate the targeted microvasculature. In practice, factors including tissue motion, probe motion, microbubble dose limit, imaging noise, and various physiological conditions (e.g., slow microvasculature perfusion) will limit the total available numbers of microbubbles for super-resolution processing. These factors can result in discontinuous microvasculature depictions with missing microvasculature structures and unreliable microvasculature flow speed measurements.

SUMMARY OF THE DISCLOSURE

The present disclosure addresses the aforementioned drawbacks by providing a method for super-resolution imaging of microvessels using an ultrasound system. Ultrasound data that were acquired with an ultrasound system from a region-of-interest in a subject in which a microbubble contrast agent was present when the ultrasound data were acquired are provided to a computer system. Microbubble signal data are generated with the computer system by isolating microbubble signals in the ultrasound data from other signals in the ultrasound data. Microbubbles are localized in the microbubble signal data by processing the microbubble signal data with the computer system to determine spatial locations associated with microbubbles in the microbubble signal data, thereby generating localized microbubble data. The localized microbubble data are input to a Kalman filter configured to at least one of correct or smooth microbubble movement trajectories in order to generate Kalman-filtered microbubble data. A super-resolution microvessel image is produced based at least in part on the Kalman-filtered microbubble data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for super-resolution imaging with ultrasound in which a Kalman filter-based microvessel inpainting technique is used to facilitate robust super-resolution imaging with limited or otherwise missing microbubble signals. The systems and methods described in the present disclosure can be combined with any suitable microbubble tracking method, including local or global microbubble tracking methods. The locations of a single microbubble that can be tracked in N consecutive frames can be used as inputs to the Kalman filter. The Kalman filter can be configured with multiple different states and a suitable transition function.

As one example, the Kalman filter can be configured with four states (e.g., lateral microbubble displacement, $d_x$; axial microbubble displacement, $d_z$; lateral flow speed, $v_x$; and axial flow speed, $v_z$) and a linear transition function, such as $d(t)=d(t-1)+v(t-1)\Delta t$. After Kalman filtering, the estimated microbubble locations with flow speed higher than a preset speed limit are rejected, followed by a microbubble trajectory inpainting process based on an interpolation, such as a spline interpolation. The interpolation factor can be adaptively determined by the local microbubble flow speed.

To achieve super-resolution ultrasound imaging, a common strategy is to create isolated point sources of microbubbles, the center locations of which are then used to form a super-resolution image. Previous super-resolution methods facilitated microbubble isolation by diluting the microbubble solutions, or by using high frame-rate ultrasound to monitor the "blinking" events of microbubbles, which can isolate individual microbubble signals from a crowd of microbubbles. In both of these methods, microbubble tracking and accumulation can be susceptible to noise and tissue motion in in vivo imaging. Using the systems and methods described in the present disclosure, a series of processing and inpainting methods are used to enhance ultrasound super-resolution imaging quality and to improve the accuracy of microbubble tracking.

Figure 1:
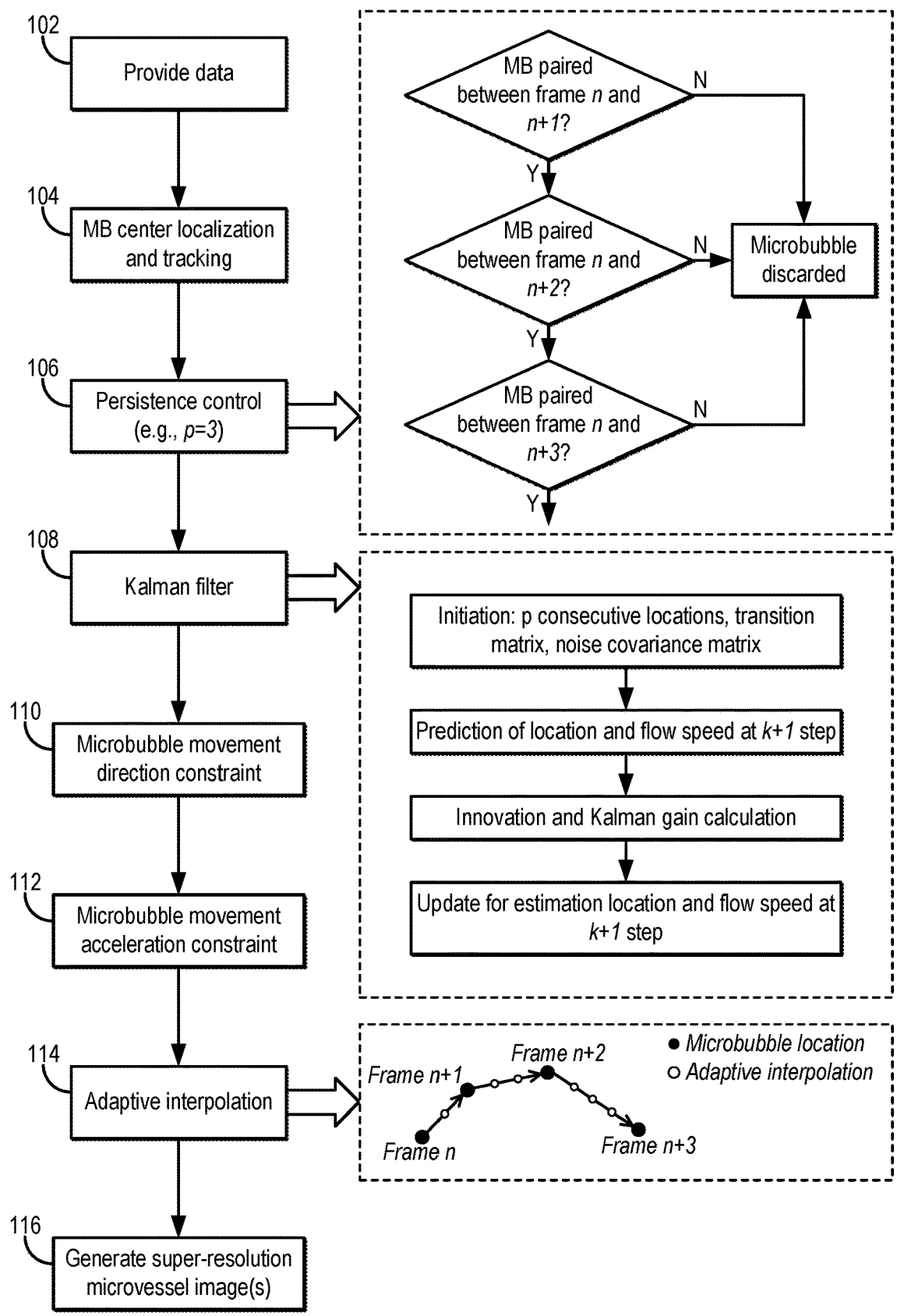
FIG. 1 is a flowchart setting forth the steps of an example method for generating super-resolution images of microvasculature using ultrasound imaging an Kalman filter-based inpainting.

Referring now to FIG. 1, a flowchart is illustrated as setting forth the steps of an example method for using an ultrasound system to produce super-resolution images of microvessels in a subject who has been administered a microbubble contrast agent. In general, super-resolution refers to a resolution that is enhanced relative to the resolution attainable with the imaging system. For instance, super-resolution ultrasound images can refer to images with resolution that is finer than the diffraction limit of ultrasound.

The method includes providing ultrasound data to a computer system, as indicated at step 102. In some embodiments, providing the ultrasound data to the computer system can include retrieving previously acquired ultrasound data from a memory or other data storage, which may be a part of or separate from the computer system. In some other embodiments, providing the ultrasound data can include acquiring such data with an ultrasound system and providing the acquired data to the computer system, which may be a part of or separate from the ultrasound system.

The ultrasound data can be ultrasound radiofrequency data, ultrasound in-phase quadrature ("IQ") data, or the like. In general, the ultrasound data contains one or more spatial dimensions, which may include a lateral dimension, an axial dimension, an elevational dimension, a temporal dimension, and combinations thereof. For instance, the ultrasound data can contain two spatial dimensions, such as the lateral and axial dimensions. The ultrasound data may also contain a temporal dimension, such as a dimension in slow time (i.e., the temporal direction along which multiple ultrasound signals are collected).

As stated above, the ultrasound data are acquired from a subject who has been administered a microbubble contrast agent. In some embodiments, different microbubbles (e.g., microbubbles with different sizes) with different resonant ultrasound frequencies can be used for imaging, so that by selecting a specific ultrasound frequency (e.g., either transmit or receive at a specific frequency), only a subgroup of selected microbubbles will be imaged, thereby forming ultrasound data containing isolated microbubble sources. As another example, an ultrasound pulse that has sufficient energy to rupture a certain number of microbubbles can be used, wherein the ruptured microbubbles then release the free gas bubbles from the microcapsule and generate ultrasound signals that have different amplitude than the intact microbubbles. This effectively creates isolated microbubble sources that can be used for super-resolution imaging. As another example, using an ultrafast plane wave imaging acquisition mode, microbubble movement, disrupture, and minute phase variations may manifest in the form a "blinking" event, which can be sensitively detected with ultrafast imaging. These blinking events can serve as isolated microbubble sources for super-resolution imaging. In some cases, a post-processing spatiotemporal filter (e.g., a high-pass filter-based clutter filter or a spatiotemporal singular-value-decomposition (SVD)-based clutter filter) can be used to extract the blinking microbubble signal.

The microbubble signal can be obtained from both the linear and nonlinear components of the ultrasound wave. The linear component is typically at the fundamental frequency of the applied ultrasound wave, while the nonlinear component can be at both the harmonic frequencies of the applied ultrasound wave, at the fundamental frequency of the applied ultrasound wave, at the ultraharmonic component of the applied ultrasound wave (e.g., 1.5 times of the fundamental frequency), the subharmonic component of the applied ultrasound wave (e.g., 0.5 times of the fundamental frequency), or combinations thereof. For instance, the nonlinearity introduced by amplitude-modulation-base imaging methods can be at the fundamental frequency. For either linear or nonlinear imaging, the above-mentioned spatiotemporal clutter filter can be used to enhance the extraction of isolated microbubble signals.

Microbubbles are localized in the microbubble signal data, as indicated at step 104. In general, this process includes identifying locations in each time frame of the microbubble signal data at which microbubbles are located. For instance, the center location of each isolated microbubble signal is located, such that the movement of the microbubble can be tracked through time. The center location of the localized microbubbles can also be used to construct super-resolution microvessel images and to track the movement of the microbubbles to calculate hemodynamics measurements, such as blood flow speed.

Persistence control is applied to the localized microbubble signals to facilitate robust microbubble tracking, as indicated at step 106. As one example, the persistence control techniques described in PCT Application No. PCT/US/18/035147, which is herein incorporated by reference in its entirety, can be implemented. The persistence control counts a microbubble signal as reliable when the same microbubble can be paired in p consecutive frames to be counted as a reliable microbubble signal. Microbubble signals that are counted as reliable can be used for the final microbubble signal accumulation step to generate microvessel density and microvessel flow speed images. As a non-limiting example, for p=3, the same microbubble has to be paired between frame n and frames n+1, n+2, and n+3, respectively, as illustrated in the yellow dashed box in FIG. 1. The locations of a single microbubble that is tracked in p consecutive frames can be used as inputs to the Kalman filter.

As indicated at step 108, the microbubble location data are then input to a Kalman filter that is suitably configured to smooth microbubble movement trajectories for more robust microvessel density maps and more reliable microvessel flow speed estimation. The Kalman filter may be a linear Kalman filter or a nonlinear Kalman filter (e.g., an unscented Kalman filter, an extended Kalman filter).

In general, a Kalman filter is an algorithm that uses a series of measurements observed over time, which contain statistical noise and measuring inaccuracies, to predict the status of variables. By estimating a joint probability distribution over the variables for each timeframe, Kalman filtered measurements can be more accurate than those based on a single measurement alone. For a stochastic dynamic system, the state of the system, $X_k$, and its observation, $Y_k$, at time k are as follows, $$X_k = F_{k-1} X_{k-1} + W_{k-1} \quad (1);$$

$$Y_k = H_k X_k + Z_k \quad (2).$$

The covariance of noise $W_k$ and $Z_k$ is $Q_k$ and $R_k$, respectively. The predicted system state at k+1 timeframe is given by, $$\hat{X}_{k+1|k} = F_k \hat{X}_{k|k-1} \quad (3);$$

$$E_{k+1|k} = F_k E_{k|k-1} F_k^T + Q_k \quad (4);$$

where $\hat{X}_{k|k}$ is an estimate of system state at time k based upon the observations $Y_0, \ldots, Y_{k-1}$, and $E_{k|k} = \text{cov}(X_k - \hat{X}_{k|k})$ is an error covariance matrix.

The innovation, $I_k$, which defines the difference between observation and prediction, and its covariance can be calculated as, $$I_k = Y_k - H_k \hat{X}_{k+1|k} \quad (5);$$

$$S_k = H_k E_{k+1|k} H_k^T + R_k \quad (6).$$

Then, the Kalman gain is given by, $$K_k = E_{k+1|k} H_k^T S_k^{-1} \quad (7).$$

The estimated system state, $\hat{X}_{k+1|k+1}$, and error covariance, $E_{k+1|k+1}$, are updated by the following:

$$\hat{X}_{k+1|k+1} = \hat{X}_{k+1|k} + K_k I_k \quad (8);$$

$$E_{k+1|k+1} = (Id - K_k H_k) E_{k+1|k} \quad (9).$$

Here, the Kalman filter is configured to be applied to super-resolution imaging to correct and smooth the microbubble movement trajectory for more robust microvessel density maps and more reliable microvessel flow speed estimation. For the super-resolution imaging system, the real microbubble positions, $X(t)$, and the observed microbubble positions, $Y(t)$, are, $$X(t+1) = FX(t) + W(t) \quad (10);$$

$$Y(t) = HX(t) + V(t) \quad (11).$$

One example implementation of microbubble trajectory correction and speed estimation with Kalman filter is as follows:

$$\begin{pmatrix} x_1(t) \\ x_2(t) \\ dx_1(t) \\ dx_2(t) \end{pmatrix} = \begin{pmatrix} 1 & 0 & 1 & 0 \\ 0 & 1 & 0 & 1 \\ 0 & 0 & 1 & 0 \\ 0 & 0 & 0 & 1 \end{pmatrix} \begin{pmatrix} x_1(t-1) \\ x_2(t-1) \\ dx_1(t-1) \\ dx_2(t-1) \end{pmatrix} + \begin{pmatrix} w_1(t-1) \\ w_2(t-1) \\ dw_1(t-1) \\ dw_2(t-1) \end{pmatrix}. \quad (12)$$

The new position, $(x_1(t), x_2(t))$ is the old position $(x_1(t-1), x_2(t-1))$ plus velocity $(dx_1(t-1), dx_2(t-1))$ plus noise, w. The observed position of microbubbles is $(y_1(t), y_2(t))$, where:

$$\begin{pmatrix} y_1(t) \\ y_2(t) \end{pmatrix} = \begin{pmatrix} 1 & 0 & 0 & 0 \\ 0 & 1 & 0 & 0 \end{pmatrix} \begin{pmatrix} x_1(t) \\ x_2(t) \\ dx_1(t) \\ dx_2(t) \end{pmatrix} + \begin{pmatrix} v_1(t) \\ v_2(t) \end{pmatrix}. \quad (13)$$

The setup for super-resolution imaging using Eqns. (12) and (13) can then be integrated to the recursion algorithm described in Eqns. (3)-(9) for Kalman filtering. After the correction steps, a Kalman smoother can be applied to the Kalman-filtered data to further reject the outlier data points. The previous steps (Eqns. (12) and (13)) can be considered a forward Kalman filtering, where only data observed in the past (e.g., t=0, 1, . . . , t-1) are used. For the Kalman smoother, filtering is done backwards in time using all of the observed data (e.g., t=0, 1, . . . , T) and all the data filtered by the forward Kalman filter. False microbubble trajectories and flow speed can be reliably rejected by the Kalman filter process. One example implementation of a Kalman filter is shown in the green box of FIG. 1.

After Kalman filtering, two constraints can be applied to further improve the robustness of microbubble tracking and flow speed calculation. A microbubble movement direction constraint can be applied at step 110 and a microbubble movement acceleration constraint can be applied at step 112.

The movement direction constraint requires the microbubbles, within the p consecutive frames in which the microbubbles are persistently paired, to not change movement directions greater than a predefined threshold. The movement angle of a microbubble from location n to location n+1 can be given as $\alpha_n$, with the location n as the origin of the coordinate. Similarly, the movement angle of a microbubble from location n+1 to location n+2 can be given as $\beta_{n+1}$, with the location n+1 as the origin. The movement direction constraint restricts a microbubble to not change its movement direction by more than a threshold angle $\theta_{thr}$ with respect to its previous trajectory, and can be expressed as:

$$\Delta \theta_n = |\beta_{n+1} - \alpha_n| < \theta_{thr} \quad (14);$$

The movement direction constraint rejects the microbubbles with one or more moving angles $\Delta \theta_n$ greater than a predefined threshold, $\theta_{thr}$. For example, such a threshold can be $\pi/2$ (i.e., one quadrant of the Cartesian coordinate).

For the movement acceleration constraint, sharp accelerations are typically caused by false microbubble signals, which produce very high microbubble/blood flow speed estimates. To reject these false microbubble signals, an acceleration constraint can be imposed on the measured microbubble trajectory. This constraint can be given by:

$$a = \frac{|v_{n+1} - v_n|}{1/FR} < a_{thr} \text{ for } n = 1, 2, \ldots, p-1; \quad (15)$$

where $v_{n+1}$ and $v_n$ are the post-Kalman filtered microbubble velocities in two consecutive frames, FR is the frame rate, a is the accelerations, and $a_{thr}$ is the threshold acceleration value, which in some instances may indicate the maximum absolute value of acceleration allowed. As one non-limiting example, a threshold value of $a_{thr}=1000$ mm/s$^2$ can be used.

After applying the Kalman filter and the above-described constraints, the remaining microbubble signals can be used to reliably inpaint the tissue microvasculature. To effectively inpaint the missing data points on the trajectory of microbubble propagation, an adaptive interpolation method can be used for the inpainting process, as indicated at step 114. Instead of using a fixed interpolation factor, the interpolation factor can be adaptively determined by the estimated flow speed at each microbubble location. A fast-moving microbubble will lead to wider gaps between adjacent detected microbubble locations, and thus may need a higher interpolation factor to fill in the gap between the adjacent detected microbubble locations. A slow-moving microbubble will lead to a smaller gap between the adjacent microbubble locations and therefore may need a lower interpolation factor to fill the gap. As a non-limiting example, illustrated in the purple box in FIG. 1, four consecutive locations of a microbubble are depicted with red dots. If the microbubble flow speed between locations at frame n and frame n+1 is V, and between frame n+1 and frame n+2 is 2V (i.e., twice as fast as the speed between frame n and n+1), then twice as many points will be interpolated in locations between frame n+1 and frame n+2 than in locations between frame n and n+1.

After the microbubbles have been localized and tracked in the microbubble signal data, one or more microvessel images are produced based on the localization and tracking results, as indicated at step 116. As one example, the microvessel image can include an accumulated microbubble location map throughout all of the acquisition frames. As another example, the microvessel image can include a blood flow speed map with blood speed values assigned to all the locations at which microbubbles were detected. The microvessel images can, therefore, in some instances depict microvessel density or microvessel blood flow speed. An accumulated microbubble location map depicts the number of times that a microbubble appeared at a certain location. Typically, larger vessels have more microbubbles flow through them during a given time interval, and thus will appear brighter than smaller vessels, which have fewer microbubbles flowing through them within the same time interval.

Figure 2:
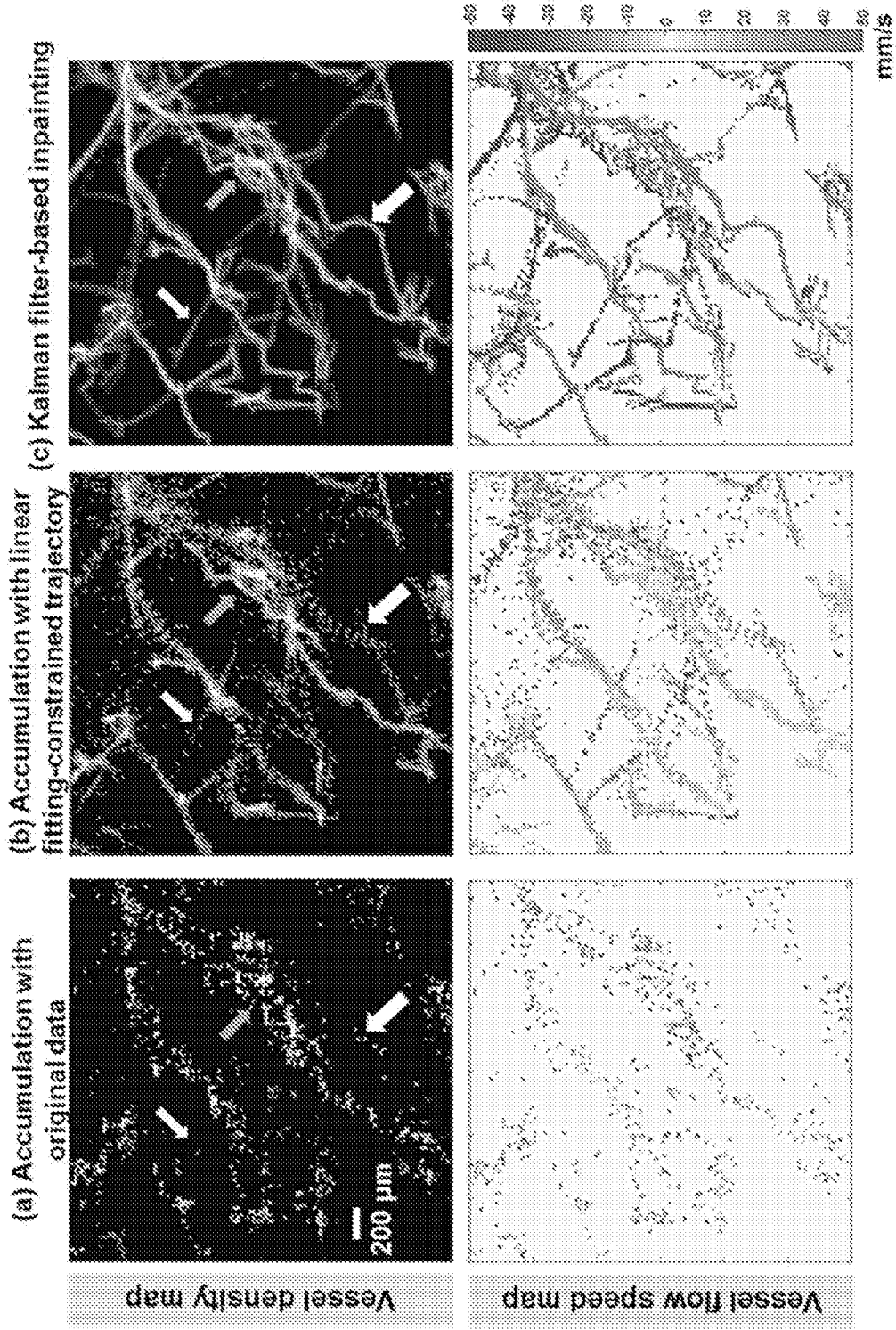
FIG. 2 shows examples of microvessel density maps (upper row) and microvessel flow maps (lower row) generated from a direct accumulation technique (first column), accumulation using linear fitting-constrained microbubble movement trajectories (second column), and using the systems and methods described in the present disclosure (third column).

The systems and methods described in the present disclosure enable marked improvement over the results from previous data accumulation and linear fitting-constrained accumulation techniques. Examples of microvessel density maps and microvessel flow maps generated with these different techniques are shown in FIG. 2. The systems and methods described in the present disclosure can robustly reconstruct vessels with missing data points, better preserve the microvessel curvature and size, and better resolve neighboring vessels than other inpainting methods, such as linear-fitting. The systems and methods described in the present disclosure can accelerate and improve robustness of super-resolution imaging by allowing robust microvessel characterization with limited or missing microbubble signals.

Figure 3:
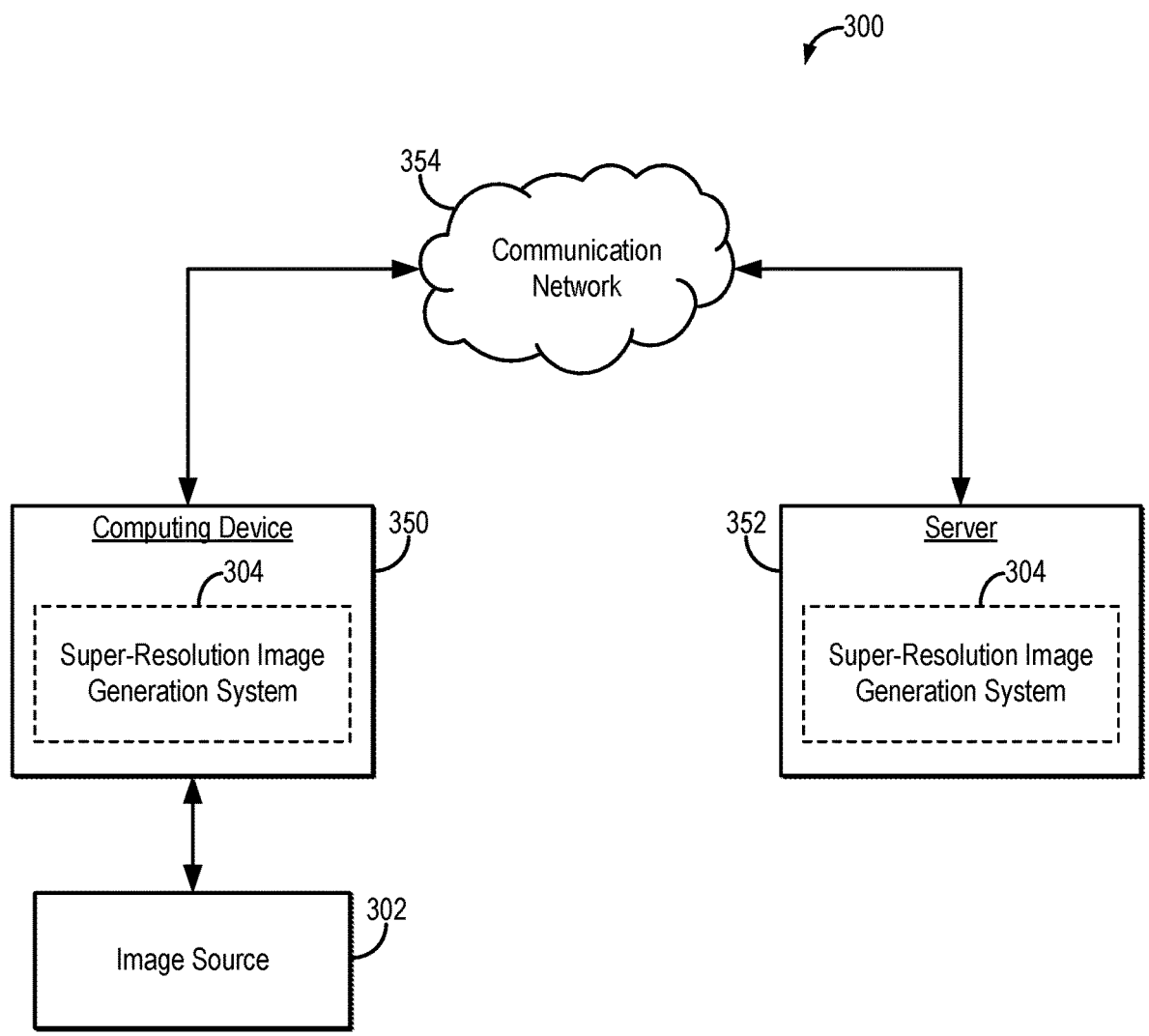
FIG. 3 is a block diagram of an example system that can implement the methods described in the present disclosure.

Referring now to FIG. 3, an example of a system 300 for generating super-resolution microvessel images in accordance with some embodiments of the systems and methods described in the present disclosure is shown. As shown in FIG. 3, a computing device 350 can receive one or more types of data (e.g., ultrasound data) from image source 302, which may be an ultrasound image source. In some embodiments, computing device 350 can execute at least a portion of a super-resolution image generation system 304 to generate super-resolution microvessel images from data received from the image source 302.

Additionally or alternatively, in some embodiments, the computing device 350 can communicate information about data received from the image source 302 to a server 352 over a communication network 354, which can execute at least a portion of the super-resolution image generation system 304 to generate super-resolution microvessel images from data received from the image source 302. In such embodiments, the server 352 can return information to the computing device 350 (and/or any other suitable computing device) indicative of an output of the super-resolution image generation system 304 to generate super-resolution microvessel images from data received from the image source 302.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as an ultrasound imaging system, another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 354 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
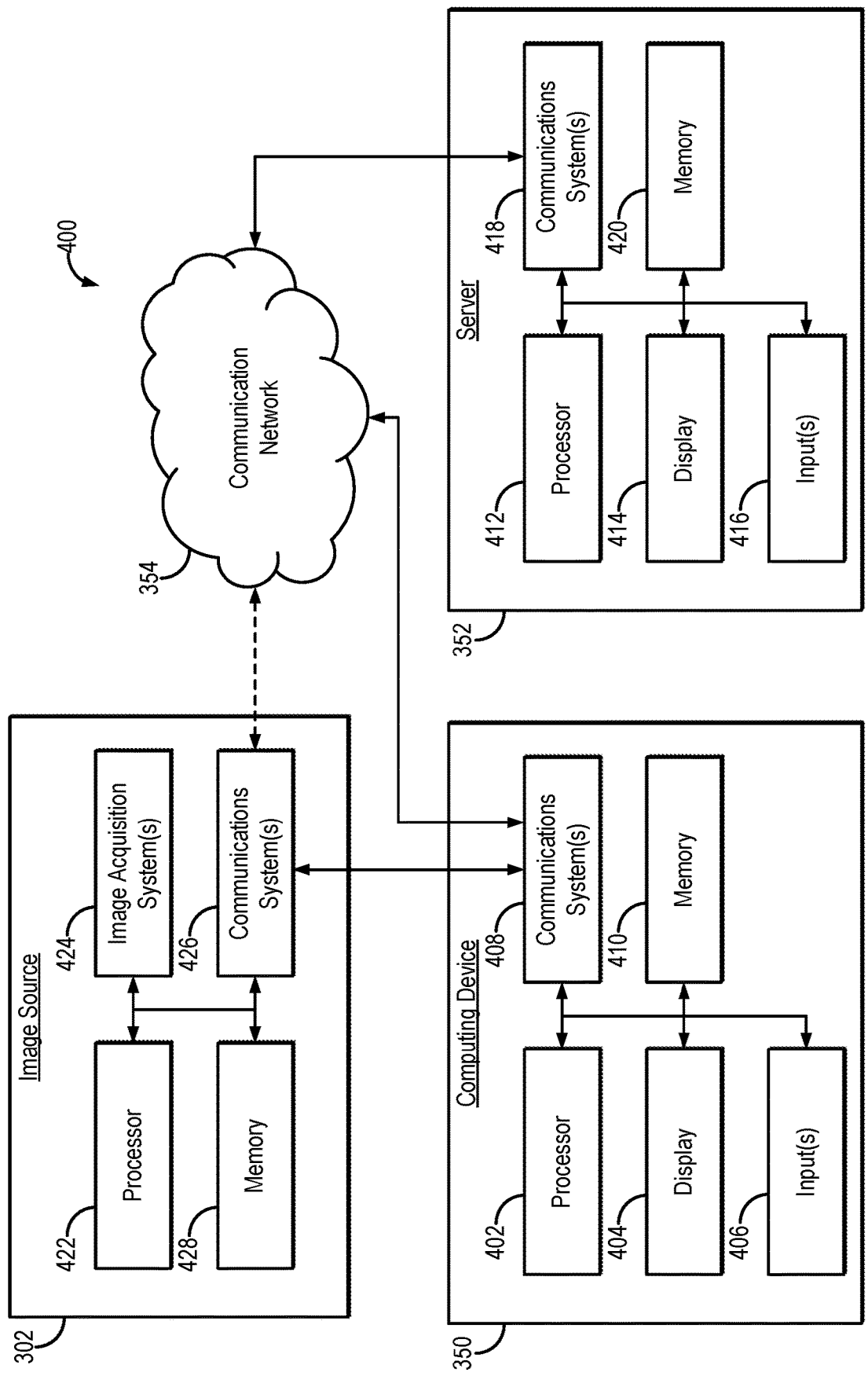
FIG. 4 is a block diagram showing hardware components that can implement the system shown in FIG. 3.

Referring now to FIG. 4, an example of hardware 400 that can be used to implement image source 302, computing device 350, and server 352 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include an ultrasound transducer. Additionally or alternatively, in some embodiments, one or more image acquisition systems 424 can include any suitable hardware, firmware, and/or software for coupling to and/or controlling operations of an ultrasound transducer or an ultrasound imaging system. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 5:
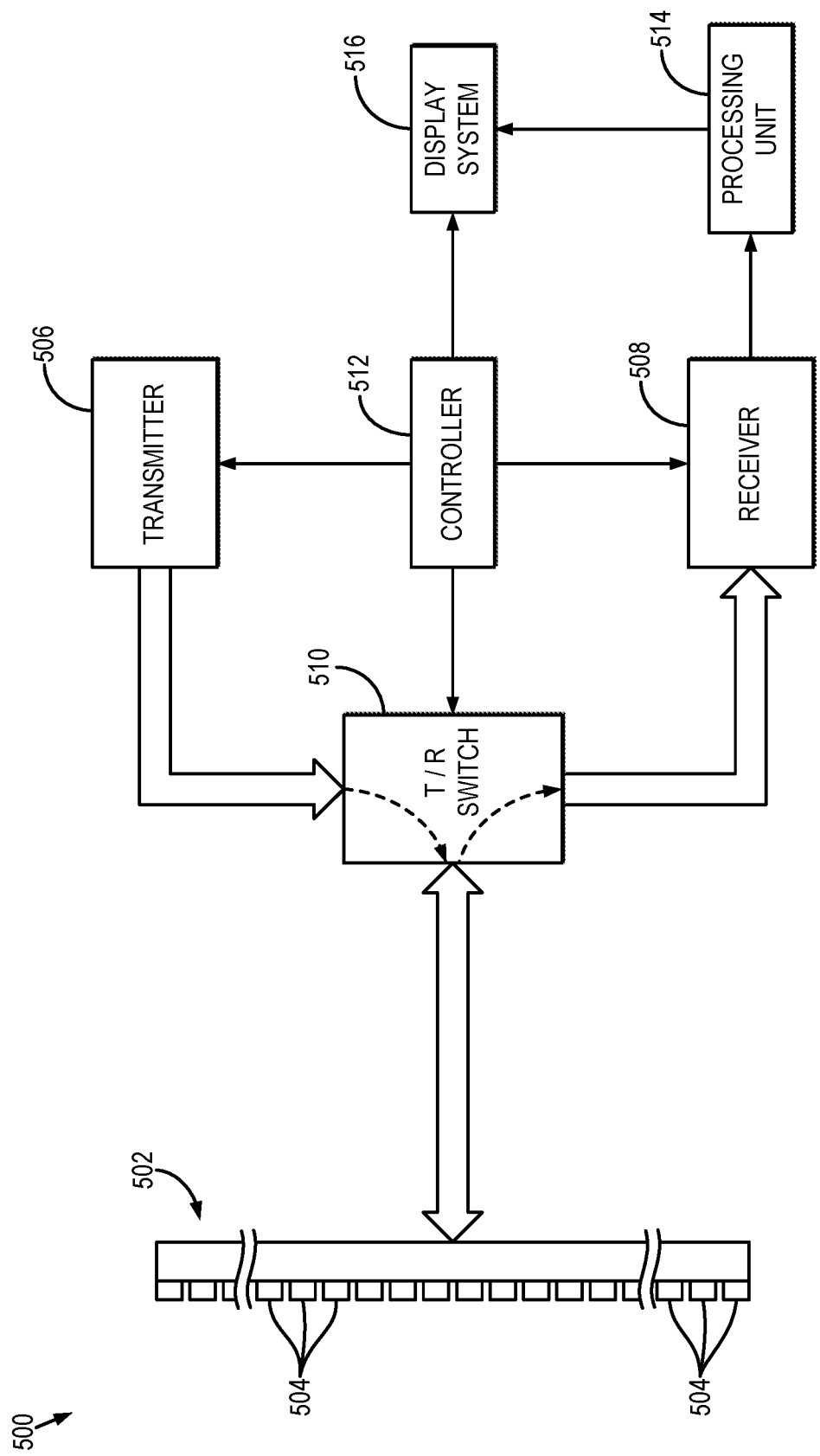
FIG. 5 is a block diagram of an example ultrasound imaging system that can be used when implementing the systems and methods described in the present disclosure.

FIG. 5 illustrates an example of an ultrasound system 500 that can implement the methods described in the present disclosure. The ultrasound system 500 includes a transducer array 502 that includes a plurality of separately driven transducer elements 504. The transducer array 502 can include any suitable ultrasound transducer array, including linear arrays, curved arrays, phased arrays, and so on. Similarly, the transducer array 502 can include a 1D transducer, a 1.5D transducer, a 1.75D transducer, a 2D transducer, a 3D transducer, and so on.

When energized by a transmitter 506, a given transducer element 504 produces a burst of ultrasonic energy. The ultrasonic energy reflected back to the transducer array 502 (e.g., an echo) from the object or subject under study is converted to an electrical signal (e.g., an echo signal) by each transducer element 504 and can be applied separately to a receiver 508 through a set of switches 510. The transmitter 506, receiver 508, and switches 510 are operated under the control of a controller 512, which may include one or more processors. As one example, the controller 512 can include a computer system.

The transmitter 506 can be programmed to transmit unfocused or focused ultrasound waves. In some configurations, the transmitter 506 can also be programmed to transmit diverged waves, spherical waves, cylindrical waves, plane waves, or combinations thereof. Furthermore, the transmitter 506 can be programmed to transmit spatially or temporally encoded pulses.

The receiver 508 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 506 and the receiver 508 can be programmed to implement a high frame rate. For instance, a frame rate associated with an acquisition pulse repetition frequency ("PRF") of at least 100 Hz can be implemented. In some configurations, the ultrasound system 500 can sample and store at least one hundred ensembles of echo signals in the temporal direction.

The controller 512 can be programmed to implement an imaging sequence using the techniques known in the art. In some embodiments, the controller 512 receives user inputs defining various factors used in the design of the imaging sequence.

A scan can be performed by setting the switches 510 to their transmit position, thereby directing the transmitter 506 to be turned on momentarily to energize transducer elements 504 during a single transmission event according to the desired imaging sequence. The switches 510 can then be set to their receive position and the subsequent echo signals produced by the transducer elements 504 in response to one or more detected echoes are measured and applied to the receiver 508. The separate echo signals from the transducer elements 504 can be combined in the receiver 508 to produce a single echo signal.

The echo signals are communicated to a processing unit 514, which may be implemented by a hardware processor and memory, to process echo signals or images generated from echo signals. As an example, the processing unit 514 can generate super-resolution microvessel images using the methods described in the present disclosure. For example, the processing unit 514 can isolate microbubble signals to produce microbubble signal data, localize microbubbles in microbubble signal data, track microbubble locations through time frames, accumulate microbubble locations, and produce microvessel images using the methods described in the present disclosure. Images produced from the echo signals by the processing unit 514 can be displayed on a display system 516.

The present disclosure has described one or more preferred embodiments, and it should be appreciated that many equivalents, alternatives, variations, and modifications, aside from those expressly stated, are possible and within the scope of the invention.

The invention claimed is:

1. A method for super-resolution imaging of microvessels using an ultrasound system, the steps of the method comprising:
   (a) providing ultrasound data to a computer system, the ultrasound data having been acquired with an ultrasound system from a region-of-interest in a subject in which a microbubble contrast agent was present when the ultrasound data were acquired;
   (b) generating microbubble signal data with the computer system by isolating microbubble signals in the ultrasound data from other signals in the ultrasound data;
   (c) localizing microbubbles in the microbubble signal data by processing the microbubble signal data with the computer system to determine spatial locations associated with microbubbles in the microbubble signal data, generating output as localized microbubble data;
   (d) inputting the localized microbubble data to a Kalman filter configured to at least one of correct or smooth microbubble movement trajectories, generating output as Kalman-filtered microbubble data; and
   (e) producing a super-resolution microvessel image based at least in part on the Kalman-filtered microbubble data;
   wherein the Kalman-filtered microbubble data are processed in step (d) using a microbubble movement direction constraint to reject microbubble locations that change movement directions over a selected number of time frames with an angle greater than a threshold value.

2. The method of claim 1, wherein the threshold value is 90 degrees.

3. The method of claim 1, wherein the Kalman-filtered microbubble data are processed in step (d) using a microbubble movement acceleration constraint to reject microbubble locations that have a movement acceleration over a selected number of time frames that is greater than a threshold value.

4. The method of claim 3, wherein the threshold value is 1,000 mm/s$^2$.

5. The method of claim 1, wherein step (e) includes using an adaptive interpolation method using an adaptively determined interpolation factor based on local microbubble flow speed.

6. The method of claim 5, wherein the interpolation factor is adaptively increased between microbubble locations associated with fast-moving microbubbles.

7. The method of claim 1, wherein the Kalman filter is a linear Kalman filter.

8. The method of claim 1, wherein the Kalman filter is a nonlinear Kalman filter.

9. The method of claim 8, wherein the nonlinear Kalman filter is an unscented Kalman filter.

10. The method of claim 1, wherein the Kalman filter is configured to correct microbubble movement trajectories using a forward Kalman filtering in which only localized microbubble signal data observed from past time frames are used.

11. The method of claim 1, wherein the Kalman filter is configured to smooth microbubble movement trajectories by filtering the localized microbubble signal data backwards in time using all observed time frames in the localized microbubble signal data.

12. A method for super-resolution imaging of microvessels using an ultrasound system, the steps of the method comprising:
(a) providing ultrasound data to a computer system, the ultrasound data having been acquired with an ultrasound system from a region-of-interest in a subject in which a microbubble contrast agent was present when the ultrasound data were acquired;
(b) generating microbubble signal data with the computer system by isolating microbubble signals in the ultrasound data from other signals in the ultrasound data;
(c) localizing microbubbles in the microbubble signal data by processing the microbubble signal data with the computer system to determine spatial locations associated with microbubbles in the microbubble signal data, generating output as localized microbubble data;
(d) inputting the localized microbubble data to a Kalman filter configured to at least one of correct or smooth microbubble movement trajectories, generating output as Kalman-filtered microbubble data; and
(e) producing a super-resolution microvessel image based at least in part on the Kalman-filtered microbubble data;
wherein the Kalman-filtered microbubble data are processed in step (d) using a microbubble movement acceleration constraint to reject microbubble locations that have a movement acceleration over a selected number of time frames that is greater than a threshold value.

13. The method of claim 12, wherein the threshold value is 1,000 mm/s$^2$.

14. The method of claim 12, wherein step (e) includes using an adaptive interpolation method using an adaptively determined interpolation factor based on local microbubble flow speed.

15. The method of claim 14, wherein the interpolation factor is adaptively increased between microbubble locations associated with fast-moving microbubbles.

16. A method for super-resolution imaging of microvessels using an ultrasound system, the steps of the method comprising:
(a) providing ultrasound data to a computer system, the ultrasound data having been acquired with an ultrasound system from a region-of-interest in a subject in which a microbubble contrast agent was present when the ultrasound data were acquired;
(b) generating microbubble signal data with the computer system by isolating microbubble signals in the ultrasound data from other signals in the ultrasound data;
(c) localizing microbubbles in the microbubble signal data by processing the microbubble signal data with the computer system to determine spatial locations associated with microbubbles in the microbubble signal data, generating output as localized microbubble data;
(d) inputting the localized microbubble data to a Kalman filter configured to at least one of correct or smooth microbubble movement trajectories, generating output as Kalman-filtered microbubble data; and
(e) producing a super-resolution microvessel image based at least in part on the Kalman-filtered microbubble data;
wherein step (e) includes using an adaptive interpolation method using an adaptively determined interpolation factor based on local microbubble flow speed.

17. The method of claim 16, wherein the interpolation factor is adaptively increased between microbubble locations associated with fast-moving microbubbles.

* * * * *